United States Patent [19]

Lennox et al.

[11] Patent Number: 5,454,807
[45] Date of Patent: Oct. 3, 1995

[54] MEDICAL TREATMENT OF DEEPLY SEATED TISSUE USING OPTICAL RADIATION

[75] Inventors: Charles D. Lennox, Hudson, N.H.; Stephen P. Beaudet, Lexington, Mass.

[73] Assignee: Boston Scientific Corporation, Natick, Mass.

[21] Appl. No.: 175,787

[22] Filed: Dec. 30, 1993

Related U.S. Application Data

[63] Continuation-in-part of Ser. No. 62,656, May 14, 1993, abandoned.

[51] Int. Cl.$^6$ .................................................. A61B 17/36
[52] U.S. Cl. ................................ 606/15; 606/14; 606/17
[58] Field of Search ........................... 606/7, 13–18; 607/89; 604/21

[56] References Cited

U.S. PATENT DOCUMENTS

| | | |
|---|---|---|
| 3,327,712 | 6/1967 | Kaufman et al. . |
| 3,471,215 | 10/1969 | Snitzer . |
| 3,858,577 | 1/1975 | Bass et al. . |
| 3,866,599 | 2/1975 | Johnson . |
| 4,273,109 | 6/1981 | Enderby . |
| 4,313,431 | 2/1982 | Frank . |
| 4,418,688 | 12/1983 | Loeb . |
| 4,418,689 | 12/1983 | Kanazawa . |
| 4,419,987 | 12/1983 | Ogiu . |
| 4,445,892 | 5/1984 | Hussein et al. . |
| 4,461,283 | 7/1984 | Doi . |
| 4,489,722 | 12/1984 | Ferraro et al. . |
| 4,503,853 | 5/1985 | Ota et al. . |
| 4,512,762 | 4/1985 | Spears . |
| 4,519,390 | 5/1985 | Horne . |
| 4,537,193 | 8/1985 | Tanner . |
| 4,608,980 | 9/1986 | Aihara . |
| 4,676,242 | 6/1987 | Doi . |
| 4,733,660 | 3/1988 | Itzkan . |
| 4,760,840 | 8/1988 | Fournier, Jr. et al. . |
| 4,768,858 | 9/1988 | Hussein . |
| 4,773,413 | 9/1988 | Hussein et al. . |
| 4,784,133 | 11/1988 | Mackin . |
| 4,808,164 | 2/1989 | Hess . |
| 4,819,630 | 4/1989 | DeHart . |
| 4,832,024 | 5/1989 | Boussignac et al. ............. 606/7 |

(List continued on next page.)

FOREIGN PATENT DOCUMENTS

| | | |
|---|---|---|
| 28 26 383.4 | 12/1979 | Germany . |
| 2147208 | 5/1985 | United Kingdom . |
| 2147209 | 5/1994 | United Kingdom . |
| WO84/04879 | 12/1984 | WIPO . |
| WO89/11834 | 12/1989 | WIPO . |
| WO93/03678 | 4/1993 | WIPO . |
| WO93/12728 | 7/1993 | WIPO . |
| WO93/18818 | 9/1993 | WIPO . |

OTHER PUBLICATIONS

Hashimoto, "Development and Early Clinical Applications of a Lateral–aiming Laser Probe", *Lasers in Med. Sci.*, 2:25–28 (1987).

Obelienius et al., "Transvenous Ablation of the Atrioventricular Conduction System by Laser Irradiation Under Endoscopic Control", *Lasers in Surgery and Medicine*, 5:469–474 (1985).

*Primary Examiner*—Stephen C. Pellegrino
*Assistant Examiner*—Michael Peffley
*Attorney, Agent, or Firm*—Fish & Richardson

[57] ABSTRACT

The invention features a treatment method of deeply seated tissue and a corresponding medical instrument. The medical instrument includes a light guide adapted to transmit light energy of a selected wavelength from a light source to a selected volume of tissue, a conduit constructed to deliver a flow of coolant from a source of coolant to a surface of the selected tissue volume through which the light energy passes in reaching the volume. The irradiation and cooling is governed by control means adapted to regulate the intensity of the light energy in respect of the flow of coolant delivered to the surface to prevent substantial damage of surface tissue while irradiating the tissue volume.

10 Claims, 7 Drawing Sheets

U.S. PATENT DOCUMENTS

| | | |
|---|---|---|
| 4,850,351 | 7/1989 | Herman et al. . |
| 4,854,320 | 8/1989 | Dew et al. . |
| 4,862,886 | 9/1989 | Clarke et al. . |
| 4,917,083 | 4/1990 | Harrington et al. . |
| 5,019,075 | 5/1991 | Spears et al. . |
| 5,057,099 | 10/1991 | Rink . |
| 5,057,104 | 10/1991 | Chess . |
| 5,061,265 | 10/1991 | Abela et al. . |
| 5,129,896 | 7/1992 | Hasson . |
| 5,151,098 | 9/1992 | Loertscher . |
| 5,163,935 | 11/1992 | Black et al. ................................ 606/7 |
| 5,169,396 | 12/1992 | Dowlatshahi et al. . |
| 5,188,634 | 2/1993 | Hussein et al. ............................ 606/7 |
| 5,190,538 | 3/1993 | Hussein et al. . |
| 5,190,540 | 3/1993 | Lee . |
| 5,207,672 | 5/1993 | Roth et al. . |
| 5,217,455 | 6/1993 | Tan . |
| 5,242,437 | 9/1993 | Everett et al. . |
| 5,242,438 | 9/1993 | Saadatmanesh ........................... 606/15 |
| 5,246,436 | 9/1993 | Abela . |
| 5,246,437 | 9/1993 | Rowe . |
| 5,257,991 | 11/1993 | Fletcher et al. ............................. 606/7 |
| 5,275,151 | 1/1994 | Shockey et al. . |
| 5,304,171 | 4/1994 | Gregory et al. . |
| 5,322,507 | 6/1994 | Costello et al. . |
| 5,370,649 | 12/1994 | Gardetto et al. . |

MEDICAL TREATMENT OF DEEPLY SEATED TISSUE USING OPTICAL RADIATION

CROSS REFERENCE TO RELATED APPLICATIONS

This application is a continuation-in-part of U.S. Ser. No. 08/062,656, filed May 14, 1993, now abandoned, the entire contents of which is hereby incorporated by reference.

BACKGROUND OF THE INVENTION

This invention relates to medical treatment of relatively deeply seated tissue using optical radiation.

Laser radiation has been widely used in medicine for performing surgical procedures or treating tissue. Laser radiation has been applied both extra-corporeally, to treat skin tissue, and intra-corporeally to treat venous or arterial walls, walls in the gastro-intestinal tract, or for the removal of plaque located on the arterial walls. The laser light has been used also for coagulation of surface wounds. Advantages of the laser light arise from the ability of delivering specific energy to the targeted, localized tissue.

Depending on the wave length of the radiation, a large amount of radiation can penetrate deeper into the tissue, but still a significant portion of the radiation is absorbed by the surface layers of the tissue. The surface absorption limits the intensity of radiation used in the tissue treatment due to the thermal damage to the surface tissue at high intensities.

Selective delivery of the laser radiation is also used as a catalyst for photochemical reactions such as in photodynamic therapy. In photodynamic therapy, a patient is injected with a drug that is designed to selectively treat certain tissues such as cancerous tissue. The drug is delivered in an inert state and is activated by light of a certain wavelength. The activated drug is limited only to the irradiated tissue which substantially eliminates possible adverse affects on other non-targeted tissue.

Laser radiation has also been used for ablating and removing specific tissue. In treatment of benign prostatic hyperplasia, the ablation process removes a portion of an enlarged prostate; this relieves the obstructive symptoms associated with the enlarged prostate. In the treatment process, the laser light heats the tissue to about 100° C. until the irradiated tissue is destroyed, and the destroyed tissue is later discharged from the body.

In treatment of ventricular tachycardia (i.e., disorder of electrical control signals within the heart), the laser light is used to target and destroy specific myocardial tissue in order to remedy the irregularity of the electrical signals. Based on detailed electro-physiological mapping of the myocardial tissue, by destroying the tissue that carries the abnormal electrical signals, the normal rhythm is restored.

In the above-described procedures, named as some examples, it is necessary to irradiate, with a sufficient dose of light, tissue located below surface accessible by external laser radiation. Due to relatively large doses of light needed for the treatment, in many cases the treatment of the below surface tissue has been difficult since the surface tissue is damaged in the process.

SUMMARY OF THE INVENTION

The invention enables treatment of deeply lying tissue using UV, visible or infra-red radiation while preventing substantial damage to the surface tissue. While the radiation is applied, the surface tissue is cooled with a stream of fluid that prevents excessive tissue heating and related undesirable radiation damage. For example, in photodynamic therapy, the surface cooling enables higher radiation power to be applied to a targeted tissue region located below the tissue surface. In treatment of the benign prostatic hyperplasia, the higher optical powers enable treatment and ablation of the deeper seated tissue. In the photocoagulation treatment, the invention enables coagulation of tissue seated deeper than the surface layers while substantially preserving the surface tissue. The same advantages are observed in the treatment of ventricular tachycardia or other medical conditions. In addition to preserving the surface tissue, the cooling fluid may cool the optical fiber, optical elements and the tip of the laser delivery system.

The invention features a laser irradiation instrument having a forward irradiation embodiment, which emits light in forward direction from a catheter tip, or a side irradiation embodiment that utilizes a mirror, a prism or other optical elements for side emission. The mirror may be a convex mirror, a concave mirror, or a flat mirror adapted to form and deliver a laser beam of a selected size to the targeted tissue.

The invention includes a wet cooling field, wherein the coolant is directly in contact with the tissue surface, or a dry cooling field, wherein the laser tip is located in a balloon with its wall pressed against the surface of the targeted tissue. The cooling fluid circulates inside of the balloon pressed against the surface tissue to cause both, cooling of the balloon and the surface tissue cooling. In addition, the balloon may provide a medium that effectively matches the refractive index of the tissue; this reduces the amount of reflected light from the tissue surface.

In another aspect, the invention features a medical instrument for irradiating tissue including a light guide adapted to transmit light energy of a selected wavelength from a light source to a selected volume of tissue; a conduit constructed to deliver a flow of coolant from a source of the coolant to a surface of the selected tissue volume through which the light energy passes in reaching the volume; and control means adapted to regulate intensity of the light energy in respect of the flow of coolant delivered to the surface to prevent substantial damage of surface tissue while irradiating the tissue volume.

Preferred embodiments of this aspect of the invention may include one or more of the following features.

The light guide of the medical instrument includes an optical fiber located within a catheter that comprises a flexible catheter body having proximal and distal ends and being capable of introduction into a lumen of a human body, the conduit located within the catheter body, a proximal connector, connected to the proximal end, adapted to introduce the coolant to the conduit and the light to the optical fiber, and a distal assembly, located near the distal end, adapted to introduce the coolant to the surface tissue and the light from the fiber to the irradiated tissue volume.

The catheter further includes a balloon located around the distal assembly and, when inflated, adapted to press its wall against the surface. The balloon is constructed to cool the surface tissue while the coolant directed toward the surface being contained within the balloon.

The catheter may be introduced to a body lumen directly or by using a guiding catheter or an endoscope.

The conduit is located coaxially around the optical fiber within the catheter body to enable cooling of the optical fiber.

The distal assembly of the instrument includes a coolant port connected to the conduit, adapted to stream the coolant toward the tissue surface to increase a cooling rate of the surface.

The coolant port is further adapted to provide a turbulent convective cooling at the tissue surface and may also cool the distal assembly.

The light guide further includes an optical element, located in the distal assembly, adapted to orient the light beam to a desired direction. The coolant port is further adapted to cool the optical element.

The optical element may be a flat mirror, a convex mirror, a concave mirror or a prism.

The coolant is liquid or gas such as water, saline, and gaseous or liquid nitrogen, oxygen, carbon dioxide.

The medical instrument uses a laser or other light source of the wavelength in the ultra-violet range, visible range or infra-red range.

In another aspect the invention features a method of treating tissue by optical radiation including the steps of:

(a) providing a source of light energy of a selected wavelength and a source of coolant;

(b) transmitting the light energy from the light source to a selected volume of tissue;

(c) delivering a flow of coolant from the coolant source to a surface of the selected tissue volume through which the light energy passes in reaching the volume; and (d) controlling intensity of the light transmitted to the tissue in respect to the flow of coolant delivered to the surface to prevent substantial damage of surface tissue while irradiating the tissue volume.

This method may be practiced by the above-described medical instrument for irradiating tissue or by any other instrument capable of performing the above-listed steps.

The method may be, for example, used for photodynamic treatment, for therapeutic destruction of relatively deeply seated tissue, for photo-coagulation treatment.

In another aspect, the invention features a device for directing laser light from an optical fiber onto target tissue deep within a patient. The device includes an elongated catheter body constructed to be delivered from outside the patient along a narrow pathway to the target tissue inside the patient. The catheter body is constructed for high torsional rigidity and includes an inner lumen constructed to receive an optical fiber. A light directing optic is connected near the distal end of the catheter body to rotate with the catheter body. The directing optic is constructed to receive laser light from the optical fiber and direct it with respect to the fiber in dependence on the relative rotational orientation of the fiber and the optic. A coupler is connected to the proximal end of the catheter body. The coupler includes a lumen constructed to receive the fiber such that the fiber may extend through the coupler and into the catheter body. The coupler includes a locking structure to hold the fiber rotationally stationary with respect to the coupler. The coupler also includes a freely rotating attachment to the catheter body so that the catheter body and light directing optic can be rotated with respect to the fiber to vary the relative orientation of the optic and fiber to direct the laser light from the optical fiber onto target tissue.

Embodiments may include one or more of the following features. The device is constructed to direct fluid through the catheter body onto the optic by including a port on the coupler for receiving the fluid from a source and directing it into the catheter body. The catheter body includes a flow aperture in alignment with the optic for directing the fluid onto the aperture. The catheter is a single-lumen catheter and the fluid flow follows a path parallel to the fiber through the lumen. The device has a fiber alignment element near the distal end of the catheter and rotatable within the catheter, including support surfaces that align the fiber with the optic. The fiber alignment element includes fluid flow directing surfaces that direct fluid onto the optic. The optic is a mirror positioned beyond the end of the fiber. The fluid flow directing surface directs the fluid to create a flow substantially parallel to the surface of the mirror. The mirror is a flat mirror. The mirror is oriented to direct the laser light through a window in the side of the device. The window is an opening and the mirror directs the fluid through the opening. The locking structure friction-fits against the fiber to form a seal that prevents fluid from leaking from the coupler.

In another aspect, the invention features a method of treating benign prostatic hyperplasia by optical radiation by:

(a) providing a source of light energy in the form of a Nd:YAG laser that emits at a wavelength of about 1,064 μm and a source of liquid coolant which is substantially transparent at the wavelength;

(b) transmitting the light energy from the light source to a selected volume of tissue in the urethra;

(c) delivering a flow of coolant from the coolant source to a region near the selected tissue volume where the flow creates turbulent flow patterns in ambient fluids in contact with the surface; and (d) controlling intensity of the light transmitted to the tissue in the range of about 60–100 watts in respect to the flow of coolant delivered to the surface to prevent substantial damage of surface tissue while irradiating the tissue volume to denature cells below the surface.

DESCRIPTION OF THE PREFERRED EMBODIMENTS

Figure 1:
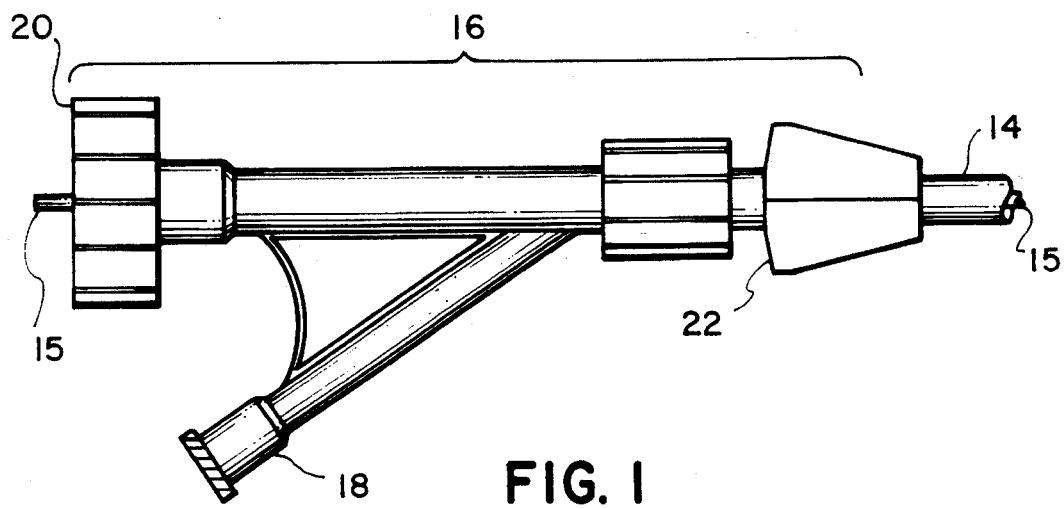
FIGS. 1, 1A, and 1B depict a laser catheter system adapted for a side illumination in accordance with the present invention.
Figure 1A:
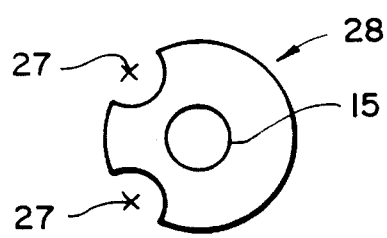
Figure 1B:
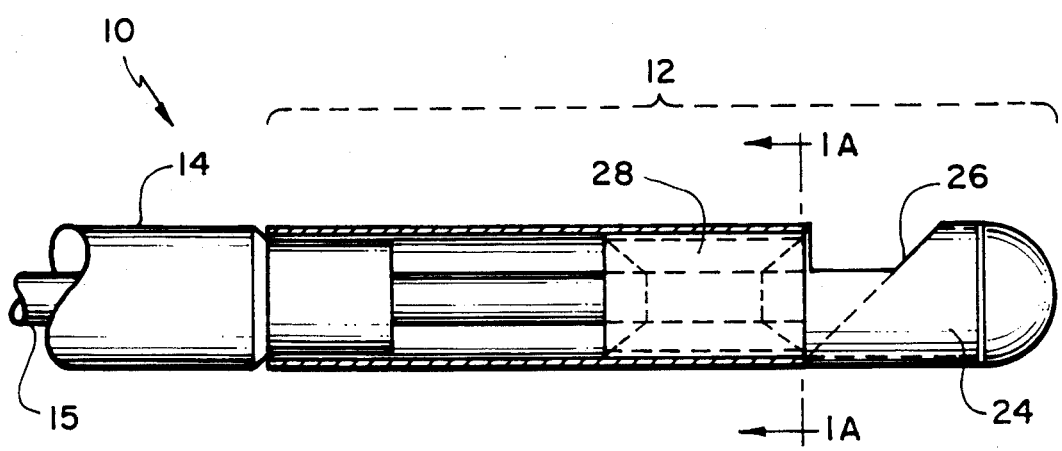

Referring to FIG. 1, the invention features a laser catheter system that includes a catheter tip assembly 12, catheter body 14 and a proximal Y-connector 16. An optical fiber 15 located inside of the catheter body extends from the proximal end to distal end of catheter 10. Located at the proximal end, Y adapter 16 includes a flush connector 18 and a touhy borst fitting 20 used for sealing optical fiber 15 in a feedthrough arrangement. The proximal Y connector further includes a thumb screw that tightens a rubber cylinder around the fiber for a tight seal. An external fluid source is attached to flash connector 18 so that the introduced fluid flows inside catheter body 14 along the entire length of optical fiber 15 to provide cooling for the fiber. Catheter tip assembly 12 includes mirror assembly 24, made of stainless steal, with a gold plated mirror surface 26. A fiber guide 28 located inside catheter tip 12 (shown in a cross-sectional view in FIG. 1A), is used for centering optical fiber 15 and for defining at least two port holes (27) adapted to deliver a stream of water to the irradiated surface tissue. Catheter tip assembly 12 is bonded to body 14 of the catheter using a cyanoacrylate adhesive. The catheter has a torque catheter design, i.e., catheter body 14 has a laminate construction of nylon, a braided stainless steel mesh, and an outer layer of nylon to increase its torsional rigidity and provide good flexibility. At the proximal end of the catheter body, a female lure fitting 22 is used for connection to the distal end of Y connector 16. The catheter size is 7 F; however, the whole assembly could be fitted to a 5 F catheter.

The invention envisions the use of different types of laser radiation, e.g., the photodynamic therapy uses a 680 nm $Ar^+$ pump dye laser or Nd YAG laser, photo-coagulation is also performed with an In YAG laser. Other longer wave lengths (e.g., Ho YAG laser of about 2.1 μm radiation or Er YAG laser of about 2.8 μm radiation) may be used, but at the longer wavelengths there is a significant water absorption. The preferred embodiment uses water for cooling but, in general, different types of coolants such as saline, liquid nitrogen or $CO_2$ may be used, wherein the cooling system of the catheter is adapted for the particular coolant.

Figure 2:
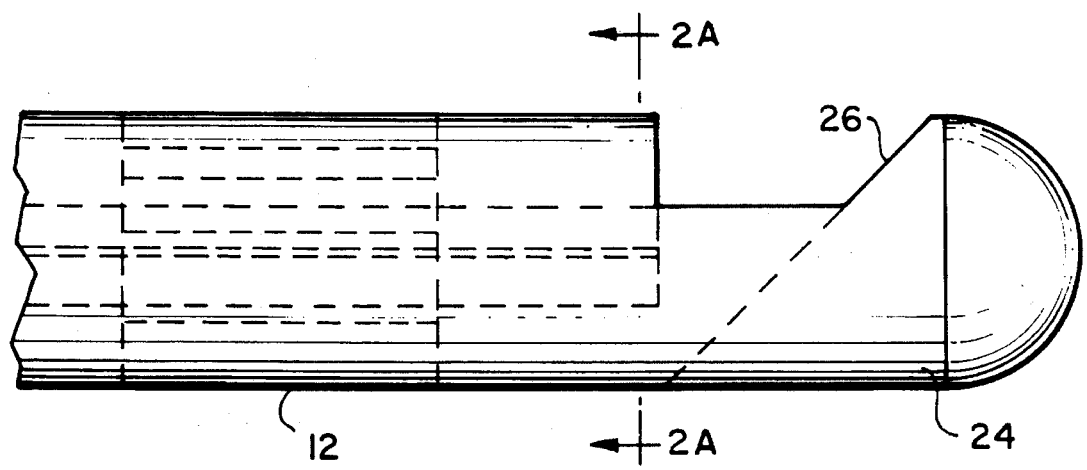
FIGS. 2 and 2A depict the distal end of the laser catheter system of FIG. 1 further including means for visualizing the treated tissue.
Figure 2A:
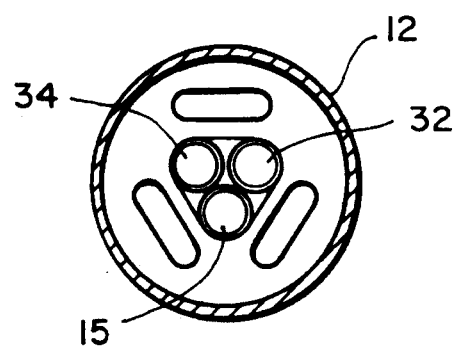

Referring to FIG. 2, an imaging system may be incorporated into the laser catheter system of FIG. 1. The imaging system includes two additional optical fibers 32 and 34 for illumination and visualization of the treated tissue, respectively. Light of a selected wave length conducted via fiber 32 illuminates the tissue surface and the light reflected from the tissue is collected by mirror 26 (or other optical system) and conducted by optical fiber bundle 34 to an optical imaging system. All three optical fibers are located in a compact design. Mirror surface 26 is again used for delivering of the treatment radiation that, in general, has a different wave length than the imaging radiation. Additional imaging optics may also be used. The proximal end of the imaging fiber is connected to a T.V. camera or a charged coupled device (CCD). The entire device is configured in a small package of about 8 to 9 F. Optical fibers 15, 32 and 34 are about 0.032" in diameter.

Figure 3A:
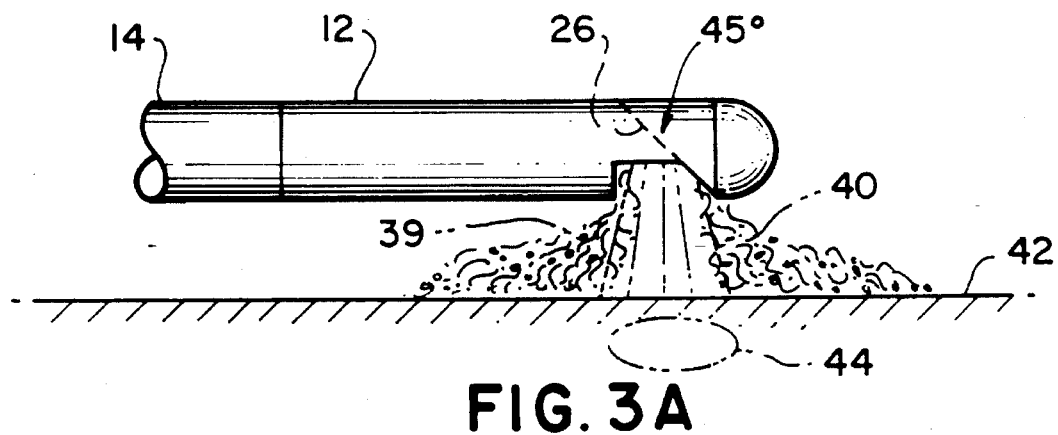
FIGS. 3A, 3B, 3C depict the laser catheter system of FIG. 1 adapted to deliver laser beam of different beam sizes.
Figure 3B:
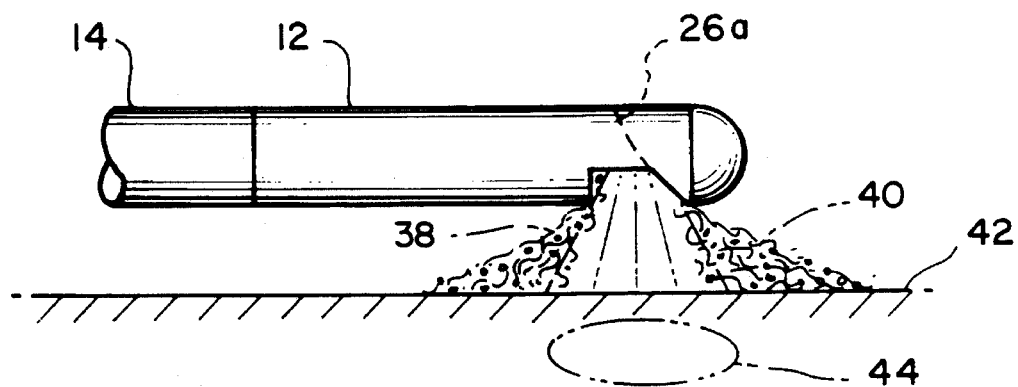
Figure 3C:
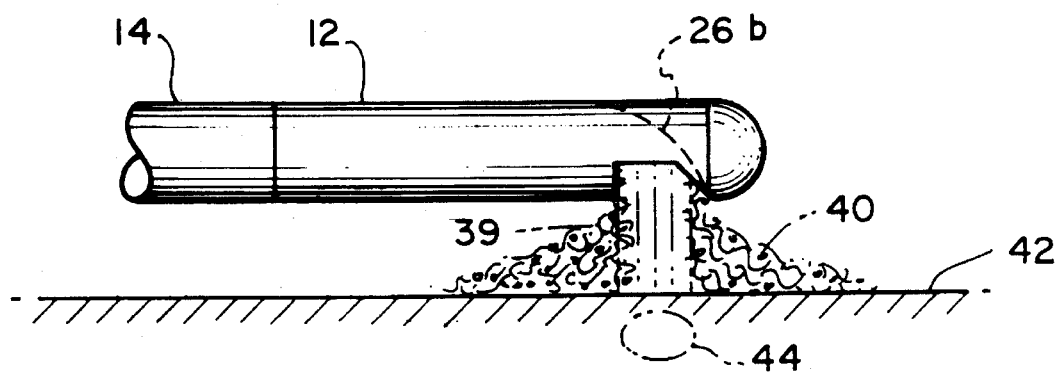

Referring to FIGS. 3A, 3B and 3C, mirror surface 26 is shaped to create different sizes of the irradiation beam at the tissue surface. Referring to FIG. 3A, a flat mirror that provides no change in the distribution angle is positioned at about 45° to direct light beam 37 to tissue surface 40. Mirror 26 is also used to deliver cooling fluid 40 (e.g., water, saline) to tissue surface 42; in this arrangement cooling fluid 40 cools both mirror 26 and surface 42. It is preferable to achieve a turbulent flow at surface 42 to ensure sufficient heat conduction away from the tissue surface. Depending on the wavelength of the laser light, deeply seated tissue 44 is irradiated with a selected dose that may be increased if the amount of cooling fluid is increased. A convex mirror 26a, shown in FIG. 3B, has the effect of spreading beam 38 and reducing the energy density delivered to the tissue. Conversely, a concave mirror 26b, shown in FIG. 3C, reduces the beam size and increases the energy density of beam 39. Thus the light dose is controlled by the intensity of the introduced light and the size of the beam correlated to the size of the treated tissue, while the depth of the treated tissue is controlled by the selected wavelength of the radiation. The amount of cooling fluid 40 delivered to the tissue surface is adjusted to achieve the desired cooling effect. Catheter assembly 10 may also include an additional lumen adapted to carry away excess cooling fluid 40.

Figure 4:
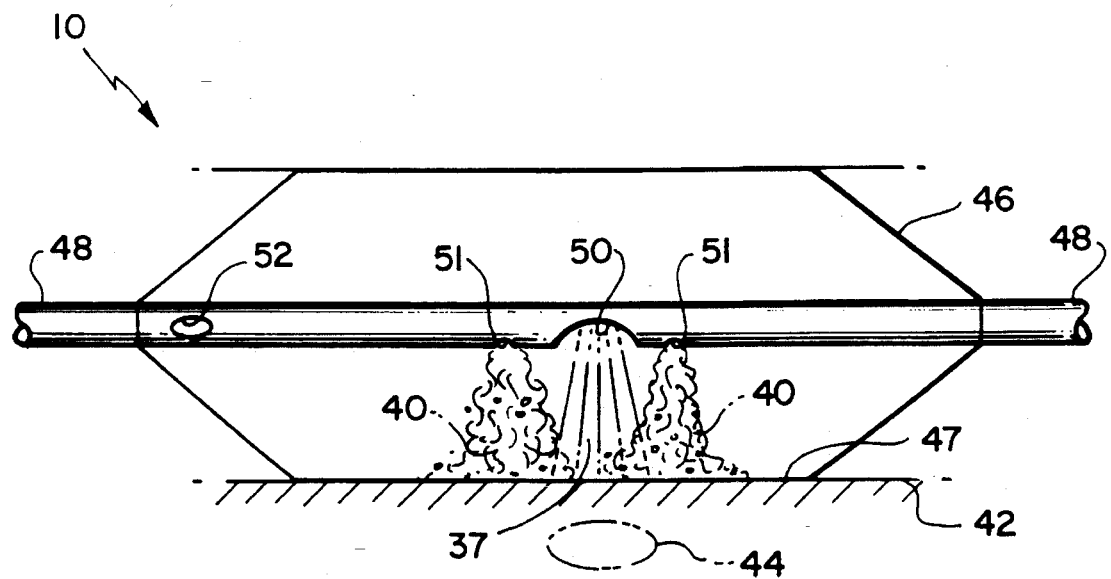
FIG. 4 depicts the laser catheter system of FIG. 1 further adapted for use in a dry cooling field.

Referring to FIG. 4, a balloon 46 located on catheter shaft 48 is used to create a dry cooling environment. Catheter shaft 48 includes an radiation port 50, coolant port 51 and a fluid return port 52. Balloon wall 47 is adapted to form an optical window for delivering the laser light. After insertion and positioning, balloon 46 is inflated so that wall 47 is in direct contact with surface 42 of the treated tissue. The cooling fluid, also used for inflation of balloon 46, protects the balloon walls from overheating that, in turn, cool the tissue. Return port 52 is connected to a return lumen located inside of catheter shaft 48 and is adapted to circulate the cooling fluid. The flow rate of the cooling fluid is adjusted to obtain a pre-determined pressure inside of balloon 46 and a desired cooling rate at surface 42. Balloon 46 is made of either PET or silicon rubber. PET forms a non-elastic balloon which assumes the pre-determined geometry, while the silicon rubber balloon is elastic and assumes the geometry of the surface it is pressed against.

In another preferred embodiment, the invention is a forward illumination system that includes a catheter 60 having proximal and distal ends. The proximal portion of catheter 60 is substantially identical with the proximal portion of catheter 10 of FIG. 1. The distal portion 67 of catheter 60, shown in FIG. 5, includes a catheter tip assembly 67 and a catheter body 62 enclosing an optical fiber 64, adapted to transmit the treatment light, and conduit 66 formed between fiber 64 and body 62 adapted to deliver cooling fluid to catheter tip 68. A proper distance between catheter tip 68 and tissue surface 78 is maintained by an adjustable standoff 70. Catheter tip 68 includes a radiation port 72, located at the distal end of optical fiber 64, and fluid delivery ports 74 adapted to direct a stream of water 76 to tissue surface 78. Radiation port 72 may be simply formed by a polished end of optical fiber 64 or may also include a beam modifying optics. The size and location of deep seated tissue 80 is targeted by selecting a suitable radiation wavelength, by properly adjusting the length of standoff 70 beyond tip 68 and by shaping the light beam at radiation port 72. The shape of delivery ports 74 and the amount of water supplied to them is adjusted to create a turbulent water flow for optimal cooling of tissue surface 78.

Figure 5:
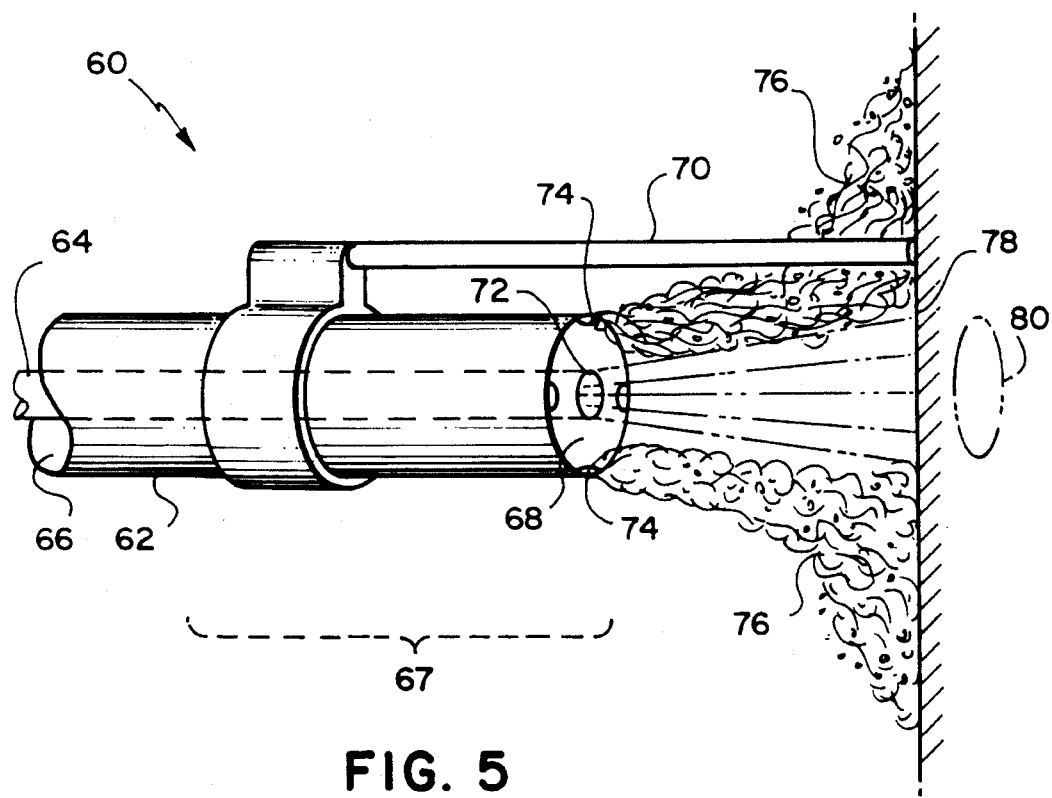
FIG. 5 depicts a laser catheter system adapted for a forward illumination in accordance with the present invention.
Figure 6:
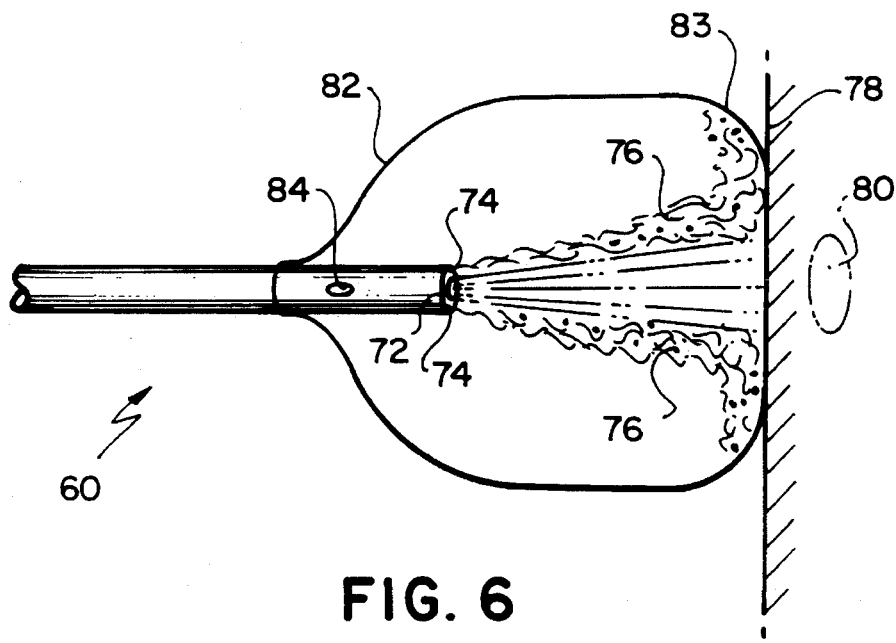
FIG. 6 depicts the laser catheter system of FIG. 5 adapted for use in a dry cooling field.

The laser catheter system of FIG. 5 may be adapted for a dry cooling field using a balloon 82, as shown in FIG. 6. Balloon 82 made of a non-elastic material, such as PET, or elastic material such as silicon rubber, is pressed against tissue surface 78 when inflated. Water stream 76 is continuously introduced to the front wall 83 of balloon 82 to provide efficient cooling of balloon wall 83 and tissue surface 78. Catheter 60 also includes an additional lumen connected to a return water port 84 and adapted to circulate the water inside balloon 82 for proper cooling.

It is worthwhile to point out that while some damage to the surface tissue may occur during the treatment, the invention prevents serious tissue damages such as charring of the tissue.

Figure 7:
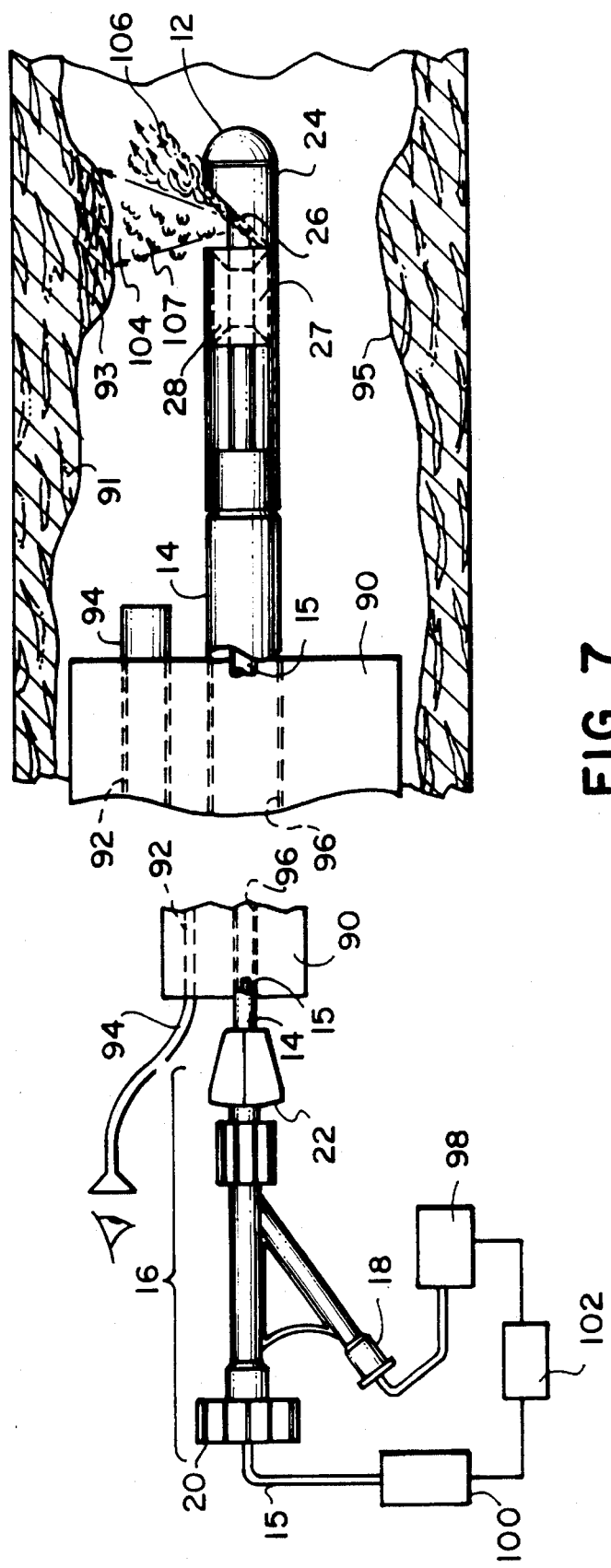
FIG. 7–7a illustrate a use of an embodiment of the invention.
Figure 7A:
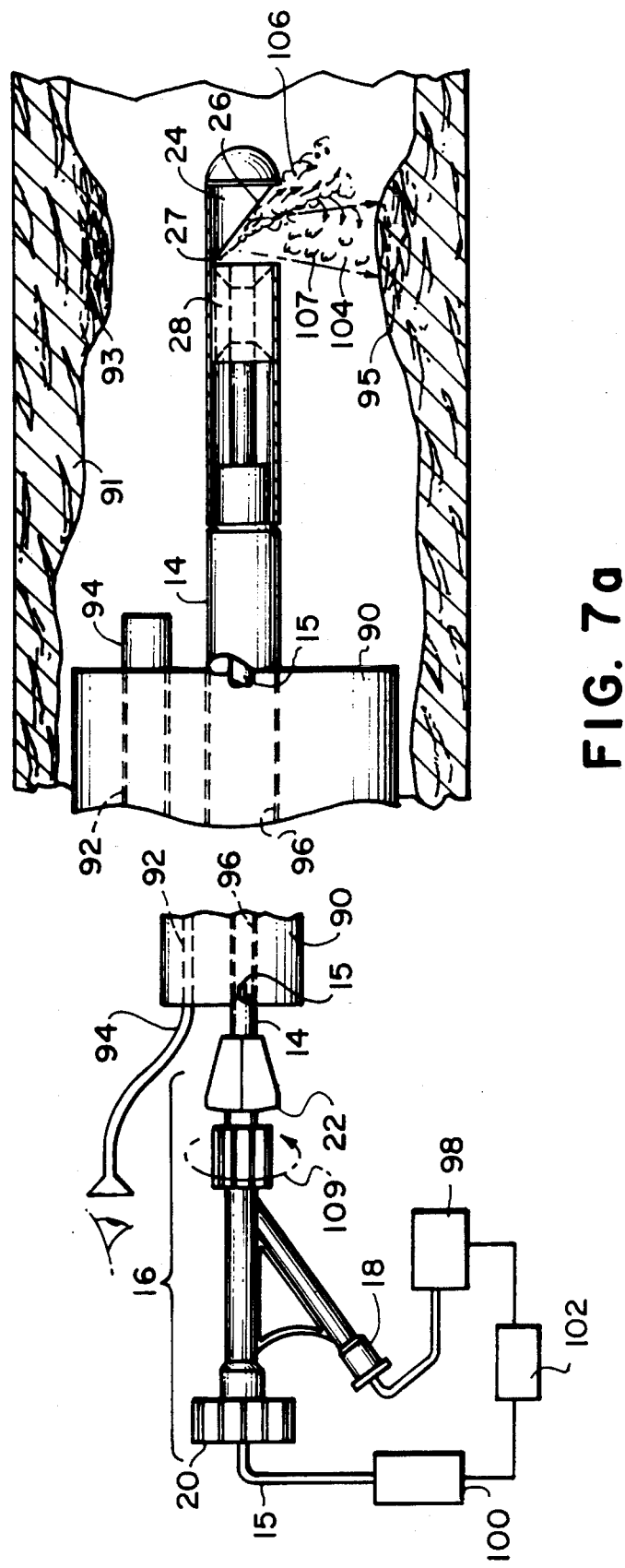

The following procedure may be followed to treat benign prostate hyperplasia. Referring to FIGS. 7 and 7a, the following equipment is used for the procedure: a rigid or flexible cystoscope 90 (outer diameter 23 F) with an 8 French working channel and a viewing channel 92 including a viewing scope 94; a laser fiber 15 having a diameter of up to about 600 microns and adapted to transmit Nd:YAG laser light; a Nd:YAG laser source 100 that emits laser light at 1.064 micron; a source 98 of saline solution, such as a sterile saline IV bag with an air trap and a pressure cuff; a subsuprabic and Foley catheter may also be provided at the physician's discretion. Finally, a system as described with respect to FIG. 1, above, is provided including a catheter 14 (about 45 cm long, about 7 French in diameter, 5 French inner diameter) with tip assembly 12 and fiber guide 28 (lumen for fiber, diameter 0.75 mm, port hole radius 0.38 mm), and a y-connector (available from Medical Profile Inc., Livonia, Mich.). The connector 16 has Tuohy-Borst fitting 20, fluid-source arm 18, and female luer fitting 22. The luer fitting 22 is connected to the y-connector by a swivel coupling so the catheter and the tip assembly can be rotated while the fiber 15 is held rotationally stationary by the Tuohy-Borst connector. (The diameter of the fiber-lumen of the fiber guide is larger than the diameter of the fiber, so the catheter and tip assembly freely rotate about the fiber.) As discussed, the catheter has high rotational fidelity. The catheter 14 (wall thickness 0.013" or 0.033 mm), is formed of a laminated nylon 12/elastomer blend-braided stainless steel mesh structure, and the attached tip assembly 12 is gold-plated stainless steel. This allows rotational forces applied to the proximal end of the catheter to be transmitted to the distal end of the catheter and tip assembly, for an easy and accurate aiming of the beam on desired target tissue. The mirror is a flat mirror at a 45° angle with respect to the fiber axis.

To perform the procedure, the laser system and fiber are prepared for delivery of laser energy as indicated in the operation manual for the particular laser system that is used. Typically, the laser fiber is prepared by cutting the cladding back about 2–5 millimeters from the distal tip. (This step may be unnecessary if the fiber manufacturer supplies the fiber prepared for use.) The laser fiber is inserted through the channel of the Tuohy-Borst fitting 20 of the Y-connector, through the catheter and into the fiber guide 28 such that the distal tip of the fiber is approximately even, axially, with the edge of the exit aperture of the fiber-lumen of the guide. The Tuohy-Borst is then tightened (clockwise), which forms a fluid-tight seal and holds the fiber rotationally stationary. The operator can check to be sure the fiber is secure by pulling on the fiber. The laser system's aiming beam is turned on and the beam aimed at a non-metallic surface to confirm proper alignment of the distal end of the fiber with the mirror 26. The saline IV bag is connected to the arm 18 of the Y-connector. The pressure cuff is placed around the IV bag.

Referring particularly to FIG. 7, the cystoscope 90 is positioned inside the urethra 91 and fluid (e.g. saline) is introduced through the cystoscope using standard techniques, to fill the area to be treated with fluid. The catheter 14 is then threaded through the working channel 96 of the cystoscope. The cuff on the saline IV bag is pressurized to about 200–300 mmHg, which is typically maintained throughout the lasing period. As illustrated, the flow of saline through the catheter is directed by the port holes 27 so a flow 106 is created substantially across and parallel to the surface of mirror 26. The port holes are permanently aligned to flow the saline across substantially the entire mirror surface. Further, since the tip assembly rotates with the catheter, the alignment of the port holes and mirror is maintained as the catheter is rotated to expose different portions of tissue by changing the orientation of the mirror. After flowing off the end of the mirror, the saline may directly cool the tissue that is exposed to the beam to a greater or less extent, depending in part on the rate of flow and on how close the device is positioned to the tissue surface. (In a typical case, the tip assembly stands off from the tissue surface during most of the operation; the distance is about one-half or one-third the width of the cystoscope, e.g. 4 mm/12 F). In the mode of operation illustrated in FIG. 7, the flow 106 does not substantially directly flush the surface of the irradiated tissue. However, turbulent back flows 107, created in the ambient fluid by the force of flow 106, may affect cooling of the tissue surface and the distal end of the fiber. This mode of fluid flow is preferred in some cases, since the tissue is not subject to a high velocity fluid stream, yet the mirror, the fiber, and the tissue can still be cooled by fluid flows.

The catheter is oriented so that the mirror 26 reflects the beam 104 at a desired target area 93, which is an area occluding the urethra. To assure proper orientation, the laser is activated to transmit a visible aiming beam, which is viewed through the cystoscope. The orientation can be adjusted by rotating the catheter by gripping the proximal end of the catheter that is outside the body or gripping the swivel portion of the y-connector that couples to the catheter (arrow 109, FIG. 7a).

After properly orienting the mirror, the treatment beam is then activated and the tissue is exposed for a prescribed amount of time and energy. In embodiments, with a flowing saline solution cooling the mirror and helping to cool the tissue surface, the power at the end of the fiber can be quite high, for example, about 60, and in some cases up to about 100 watts. The target tissue is typically exposed for only about 90 seconds and denaturation occurs to a maximum depth of about 1 cm without substantial charring of the surface.

Referring to FIG. 7a, after the target area 93 has been exposed, another portion of the lumen, for example, area 95, directly opposite the first portion, can be exposed by rotating the y-connector swivel coupling to the catheter (arrow 109), to orient the mirror 26 such that the beam is directed onto tissue area 95. After suitable exposure of the desired target areas, the system and cystoscope are removed from the body. Over time, the cells in the target areas that were denatured by the laser light are sloughed from the surface and exit the body leaving a wider lumen.

The system can also be used to treat aflictions such as urethral bleeding, clot retention, urethral strictures, incontinence, local and/or systemic infection, bladder spasms, perforation of the bladder wall or urethra, retrograde ejaculation, impotence, and damage to strictures surrounding the urinary tract. The laser power and flow of the saline cooling solution can be controlled manually by the physician as the procedure is observed through a cystoscope. Alternatively, as illustrated in FIGS. 7 and 7a, the system may also include a controller 102, e.g. a computer programmed and interfaced to automatically control the flow (e.g. bag pressure) of fluid and the laser power output to maintain cooling of the mirror and/or avoid charring of the target tissue.

Other embodiments are within the scope of the following claims.

We claim:

1. A device for laterally directing laser light from an optical fiber onto target tissue deep within a patient, comprising:

an elongated catheter body extending along an axis and constructed to be delivered from outside the patient along a narrow pathway to said target tissue inside the patient, said catheter body having high torsional rigidity and including an inner lumen for receiving an optical fiber substantially along its axis in a manner to permit rotation of said catheter body about said fiber, said catheter body further including lumenal space for receiving and directing a flow of fluid along its length, an alignment element fixed near the distal end of said catheter body and rotatable with said catheter body, said alignment element including support surfaces for receiving the distal end of said fiber and maintaining said distal end of said fiber substantially on said catheter body axis in a manner to permit rotation of said catheter body and said alignment element about said fiber, and said alignment element further including fluid flow directing surfaces that are aligned to direct fluid flow distally beyond said alignment element, a light directing optic, fixed near the distal end of said catheter body and rotatable with said catheter body and said alignment element, said light directing optic positioned to receive laser light emitted from said distal end of said fiber and fluid directed by said alignment element, and to direct said laser light and said fluid laterally onto a target arc-segment of tissue adjacent the directing optic that varies in dependence on the rotational orientation of said optic, and a coupler connected to the proximal end of said catheter body remaining outside of said patient, said coupler being constructed to direct fluid into said catheter body and to receive said fiber such that said fiber extends through said coupler and into said catheter body, said coupler further including a locking structure to hold said fiber rotationally and axially stationary and said coupler further including a rotatable attachment to said catheter body so that said catheter body, alignment element, and light directing optic can be rotated together about said fiber to vary the orientation of the optic to direct said laser light and fluid flow onto a desired target arc-segment of tissue.

2. The device of claim 1 wherein said catheter is a single-lumen catheter and said fluid flow follows a path parallel to said fiber through said lumen.

3. The device of claim 1 or 2 wherein said fluid flow directing surfaces direct said fluid to create a flow substantially parallel to the surface of the directing optic that receives said laser light.

4. The device of claim 3 wherein said directing optic is a flat mirror.

5. The device of claim 1 wherein said locking structure releasably friction fits against said fiber.

6. The device of claim 1 wherein said directing optic is a mirror.

7. The device of claim 1 wherein said fluid flow directing surfaces define a flow aperture positioned radially opposite the lateral tissue arc-segment to which said laser light and fluid are directed by said optic.

8. The device of claim 7 wherein said light directing optic is a mirror.

9. The device of any one of claims 1, 2, 6, 7, or 8 wherein said catheter body and light directing optic are sized to pass through a urethral cystoscope.

10. The device of claim 9 further including a laser power source set to deliver laser energy at energy levels in the range of about 60–100 watts.

* * * * *

UNITED STATES PATENT AND TRADEMARK OFFICE
CERTIFICATE OF CORRECTION

PATENT NO.    : 5,454,807

DATED         : October 3, 1995

INVENTOR(S)   : Charles D. Lennox et al.

It is certified that error appears in the above-identified patent and that said Letters Patent is hereby corrected as shown below:

TITLE PAGE:

In [56] References Cited, U.S. PATENT DOCUMENTS section:

"5,246,436 9/1993 Abela
     5,246,437 9/1993 Rowe"

should be

--5,246,436 9/1993 Rowe
   5,246,437 9/1993 Abela--

Col. 4, line 18, "1,064" should be --1.064--.

Col. 6, line 7, "an" should be --a--.

Signed and Sealed this

Third Day of September, 1996

Attest:

BRUCE LEHMAN

*Attesting Officer*      *Commissioner of Patents and Trademarks*